United States Patent
Yamanaka et al.

(10) Patent No.: US 7,927,567 B2
(45) Date of Patent: Apr. 19, 2011

(54) ADSORBENT, POROUS FILTER, AIR CLEANING DEVICE, METHOD OF CLEANING AIR, AND METHOD OF MANUFACTURING POROUS FILTER

(75) Inventors: Mikihiro Yamanaka, Kyoto (JP); Jun Kudo, Nara (JP); Keita Hara, Kashihara (JP)

(73) Assignee: Sharp Kabushiki Kaisha, Osaka (JP)

( * ) Notice: Subject to any disclaimer, the term of this patent is extended or adjusted under 35 U.S.C. 154(b) by 980 days.

(21) Appl. No.: 11/258,065

(22) Filed: Oct. 26, 2005

(65) Prior Publication Data

US 2006/0133975 A1 Jun. 22, 2006

(30) Foreign Application Priority Data

Dec. 20, 2004 (JP) ................................. 2004-367845
Dec. 20, 2004 (JP) ................................. 2004-367846

(51) Int. Cl.
  *B01D 53/46* (2006.01)
  *B01D 53/04* (2006.01)
(52) U.S. Cl. .................. 423/210; 423/447.1; 423/447.2; 423/447.3; 95/90; 96/108; 502/400
(58) Field of Classification Search .................. 423/210, 423/447.2, 447.1; 96/1, 153, 108; 55/350.1; 502/400; 95/90
  See application file for complete search history.

(56) References Cited

U.S. PATENT DOCUMENTS

| | | | | |
|---|---|---|---|---|
| 3,645,072 A | * | 2/1972 | Clapham | ........................ 96/153 |
| 5,310,548 A | * | 5/1994 | Tsuru et al. | .................. 424/76.3 |
| 5,332,426 A | * | 7/1994 | Tang et al. | ........................ 96/153 |
| 5,538,545 A | * | 7/1996 | Dauber et al. | ................... 96/153 |
| 6,749,826 B2 | * | 6/2004 | Alcaraz et al. | ............. 423/447.2 |
| 6,960,334 B1 | * | 11/2005 | Matsui et al. | ............... 423/447.1 |
| 7,022,158 B2 | * | 4/2006 | Seguin et al. | ...................... 95/90 |
| 7,056,455 B2 | * | 6/2006 | Matyjaszewski et al. | ... 264/29.2 |
| 2006/0093740 A1 | | 5/2006 | Park et al. | |

FOREIGN PATENT DOCUMENTS

| | | |
|---|---|---|
| AU | 2003302884 A1 | 6/2004 |
| JP | 55-44548 A | 3/1980 |
| JP | 8-173760 A | 7/1996 |
| JP | 11-216327 A | 8/1999 |
| JP | 2001-10809 A | 1/2001 |
| JP | 2001-164430 A | 6/2001 |
| JP | 2002-212838 A | 7/2002 |

(Continued)

*Primary Examiner* — Duane Smith
*Assistant Examiner* — Ives Wu
(74) *Attorney, Agent, or Firm* — Birch, Stewart, Kolasch & Birch, LLP

(57) ABSTRACT

An adsorbent including a porous member having holes and a nanostructure formed on at least a portion of a surface of the porous member, and an air cleaning device including the adsorbent. A porous filter including a porous member having holes and a nanostructure formed on at least a portion of a surface of the porous member, and an air cleaning device including the porous filter. A method of cleaning air for decomposing a hazardous substance using the porous filter and a decomposition gas including a superheated water vapor. A method of manufacturing a porous filter including the steps of growing a nanostructure on at least a portion of a surface of a porous member having holes, allowing a catalyst particle to be contained in a dispersion gas including a superheated water vapor, and spraying the dispersion gas on a surface of the nanostructure to attach the catalyst particle thereto.

7 Claims, 6 Drawing Sheets

FOREIGN PATENT DOCUMENTS

| | | |
|---|---|---|
| JP | 2004-125513 A | 4/2004 |
| JP | 2004-148304 A | 5/2004 |
| JP | 2004-148305 A | 5/2004 |
| JP | 2004-188243 A | 7/2004 |
| JP | 2004-203654 A | 7/2004 |
| JP | 2004-292310 A | 10/2004 |
| JP | 2006-136878 A | 6/2006 |
| WO | WO-00/40509 A1 | 7/2000 |

* cited by examiner

ADSORBENT, POROUS FILTER, AIR CLEANING DEVICE, METHOD OF CLEANING AIR, AND METHOD OF MANUFACTURING POROUS FILTER

This nonprovisional application is based on Japanese Patent Applications Nos. 2004-367845 and 2004-367846 filed with the Japan Patent Office on Dec. 20, 2004, the entire contents of which are hereby incorporated by reference.

BACKGROUND OF THE INVENTION

1. Field of the Invention

The present invention relates to an adsorbent, a porous filter, an air cleaning device, a method of cleaning air, and a method of manufacturing a porous filter. More specifically, the present invention relates to an adsorbent, a porous filter, an air cleaning device, a method of cleaning air, and a method of manufacturing a porous filter which can efficiently remove hazardous substances.

2. Description of the Background Art

In addition to a conventional problem of environmental pollution caused by a foul smell, a contaminant or a hazardous chemical substance which is industrially generated from a factory or a clean room, a problem of contamination of air inside a space for daily life, for example, a room or a car, by a hazardous substance such as a foul smell, a hazardous chemical substance, pollen, floating dust, or floating bacteria is becoming a big concern in recent years as demands for improved amenities increase, and therefore needs for removal of such hazardous substances are rapidly increasing. One of main reasons for such needs is that there are increasing number of people, one out of ten people for the present, who develop chemical sensitivity.

A common method for removing a hazardous substance such as a foul smell or a hazardous chemical in an environment is adsorption with an adsorbent formed with a porous material such as activated carbon or zeolite. Since conventional activated carbon has a specific surface area as small as a hundred to a few hundred $m^2/g$, however, a removal property thereof rapidly decreases after it adsorbs a certain amount of the hazardous substance, or the hazardous substance once adsorbed may be released again depending on an environmental temperature or a concentration of the hazardous substance. Therefore, fibrous activated carbon having an increased specific surface area (generally 1500-1700 $m^2/g$), for example, has been developed (see, for example, Japanese Patent Laying Open Nos. 2002-212838 and 2001-164430).

SUMMARY OF THE INVENTION

Though fibrous activated carbon as an adsorbent used to remove a hazardous chemical substance has an improved adsorption speed as compared to conventional activated carbon, it does not have a satisfactory removal property in a concentration range of the hazardous chemical substance in a ppb order, which is critical for chemical sensitivity. That is, since a unit mass of fibrous activated carbon can adsorb at most a few mg of formaldehyde, only a small area of a specific surface area larger than 1000 $m^2/g$ can be utilized to adsorb the hazardous chemical substance. In addition, the adsorption speed is such that only 0.2-0.001 mg of the hazardous chemical substance can be collected in one minute per 1 g of the adsorbent, and a concentration of the hazardous chemical substance in this situation decreases only to tens to several ppm.

In addition, since the fibrous activated carbon has an extremely short life of at most one year, it must be replaced frequently. Furthermore, the fibrous activated carbon cannot be restored and requires a high cost.

In addition, though it is expected that a property of adsorbing a hazardous substance such as a hazardous chemical substance is increased with an increased specific surface area of the adsorbent, when the specific surface area becomes larger than 2500 $m^2/g$, strength of the adsorbent decreases and a hazardous substance such as dust is generated from the adsorbent itself. In an air cleaning device using the adsorbent as a filter, the increased specific surface area of the adsorbent causes a pressure loss, and therefore problems of increased power consumption of the air cleaning device and increased noise generated from the air cleaning device further occur.

In addition, chemical modification of a pore of activated carbon of about several nm is very difficult considering an injection pressure. When measured with a mercury porosimeter, for example, an injection pressure of mercury of about 700 atm is required when a diameter of the pore is 20 nm, and the injection pressure of mercury of about 3500 atm is required when the diameter of the pore is 4 nm. Therefore, activated carbon as a base material must have a high mechanical strength for such a high injection pressure required, which also causes a problem with increasing of the specific surface area.

On the other hand, as indicated in Japanese Patent Laying-Open No. 2004-148305, a hazardous substance can also be removed utilizing a photocatalyst such as titanium oxide. Only a portion of the photocatalyst near a surface thereof, however, can decompose and remove the hazardous substance by photocatalysis, and therefore there is only a small region which can remove the hazardous substance. In addition, when the hazardous substance is decomposed on the surface of the photocatalyst, an organic substance generated by decomposition covers the surface of the photocatalyst to cause poisoning. Catalysis also does not occur when dust or dirt is attached to the surface of the photocatalyst. Furthermore, a construction of a device is limited since a light source for promoting the catalysis must be additionally provided.

An object of the present invention is to provide an adsorbent, a porous filter, an air cleaning device, a method of cleaning air, and a method of manufacturing a porous filter which can efficiently remove hazardous substances.

The present invention is an adsorbent including a porous member having a plurality of holes and a nanostructure formed on at least a portion of a surface of the porous member.

In the adsorbent of the present invention, the nanostructure may be formed with carbon.

In the adsorbent of the present invention, the porous member is preferably resistant to heat of at least 200° C.

In the adsorbent of the present invention, at least a portion of the surface of the porous member may be coated with a metal.

In the adsorbent of the present invention, at least a portion of the surface of the porous member may be coated with a magnetic material.

In addition, the present invention is an air cleaning device including the aforementioned adsorbent.

In addition, the present invention is a porous filter including a porous member having a plurality of holes and a nanostructure formed on at least a portion of a surface of the porous member.

In the porous filter of the present invention, the nanostructure may be formed with carbon.

In the porous filter of the present invention, the porous member is preferably resistant to heat of at least 200° C.

In addition, the present invention is an air cleaning device including the aforementioned porous filter.

In addition, the present invention is a method of cleaning air including the step of decomposing a hazardous substance using the aforementioned porous filter and a decomposition gas including a superheated water vapor.

In the method of cleaning air of the present invention, the decomposition gas preferably contains a decomposition acceleration gas.

Furthermore, the present invention is a method of manufacturing a porous filter including the steps of growing a nanostructure on at least a portion of a surface of a porous member having a plurality of holes, allowing a catalyst particle to be contained in a dispersion gas including a superheated water vapor, and spraying the dispersion gas containing the catalyst particle on a surface of the nanostructure to attach the catalyst particle to the surface of the nanostructure.

According to the present invention, an adsorbent, a porous filter, an air cleaning device, a method of cleaning air, and a method of manufacturing a porous filter which can efficiently remove hazardous substances can be provided.

In the present invention, the nanostructure means a structure having at least one dimension, such as a width, a length or a diameter, being at least 1 nm and less than 1000 nm.

In addition, "resistant to heat of at least 200° C." in the present invention means that the porous member is not deformed when it is heated to a temperature of at least 200° C. at 1 atmospheric pressure.

In addition, "the decomposition gas" means "a gas for decomposing the hazardous substance" in the present invention.

In addition, "the decomposition acceleration gas" means "a gas for accelerating decomposition of the hazardous substance" in the present invention.

In addition, "the dispersion gas" means "a gas for dispersing the catalyst particle" in the present invention.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
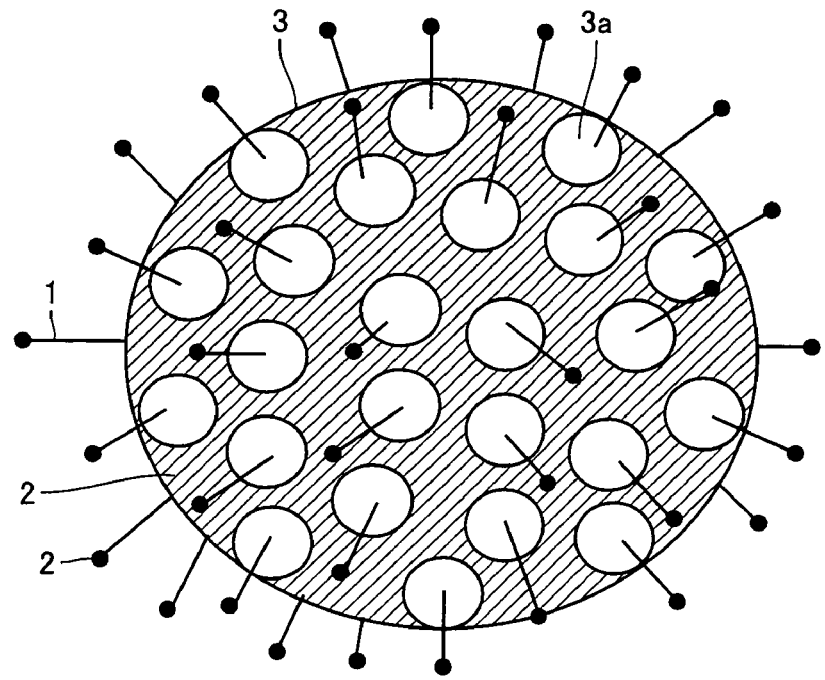
FIG. 1 is an enlarged schematic perspective view of a preferred example of an adsorbent of the present invention.

FIG. 1 is an enlarged schematic perspective view of a preferred example of an adsorbent of the present invention.

The adsorbent of the present invention includes a porous member 3 having a plurality of holes 3a, fibrous nanostructures 1 provided on an outer surface of porous member 3 and inside holes 3a and projecting from porous member 3, and catalyst particles 2 coating a surface of porous member 3 (the outer surface of porous member 3 and inner surfaces of holes 3a) and held on tips of nanostructures 1. Holes 3a may or may not penetrate porous member 3.

Nanostructure 1 may or may not have a hollow structure. Examples of a material which can be used to form nanostructure 1 include a carbon-based material such as a hollow carbon nanotube or a non-hollow carbon fiber or carbon nanowire (a fibrous carbon which is finer than a carbon fiber), a metal-based material such as Au, Ag or Ni, and a material such as $TiO_2$ or Si.

Examples of a material which can be used to form porous member 3 include a metal oxide-based material such as $Al_2O_3$, $TiO_2$, $ZrO_2$, $Nb_2O_5$, $SnO_2$, $HfO_2$, or $AlPO_4$, a silicate-based material such as $SiO_2.Al_2O_3$, $SiO_2.TiO_2$, $SiO_2.V_2O_5$, $SiO_2.B_2O_3$, or $SiO_2.Fe_2O_3$, a metal-based material formed with Pt, Ag, Au, or the like, a semiconductor-based material formed with Si or the like, a carbon-based material formed with activated carbon, an organic polymer or the like, a material derived from a living body such as diatomaceous earth or a scallop shell, and $SiO_2$. Since porous member 3 is often heated to at least 200° C. when nanostructures 1 are formed on the surface of porous member 3, porous member 3 is preferably resistant to heat of at least 200° C.

In addition, though a diameter of hole 3a formed in porous member 3 varies depending on the material forming porous member 3, when porous member 3 is formed with diatomaceous earth having a particle diameter of about 2-500 μm, for example, the diameter of the hole can be about 0.1-100 μm.

In addition, when nanostructure 1 is formed with the aforementioned carbon-based material, at least one of metals such as Fe, Ni, Co, Cr, Mo, W, Ti, Au, Ag, Cu, Pt, Ta, Al, Pd, Gd, Sm, Nd, and Dy, for example, can be used as a material to form catalyst particle 2. A diameter of catalyst particle 2 tends to control a diameter of fibrous nanostructure 1, that is, catalyst particle 2 having a smaller diameter tends to allow formation of fibrous nanostructure 1 having a smaller diameter by vapor phase epitaxy such as plasma CVD. Catalyst particle 2 has a function of accelerating growth of nanostructure 1 during formation of fibrous nanostructure 1 by the vapor phase epitaxy such as the plasma CVD.

It is expected that the adsorbent of the present invention as described above has a high adsorption property. That is, when gas including a hazardous substance is circulated at a constant speed, for example, only a small surface area of conventionally used activated carbon contacts and reacts with flowing gas per unit time, because activated carbon have to capture molecules into pores formed therein. In contrast, since most of a surface of the nanostructure formed on the adsorbent of the present invention can directly contact gas including a hazardous substance, more hazardous substance can be adsorbed and an adsorption speed also substantially increases.

Furthermore, in contrast to the pores of activated carbon, since the nanostructure formed on the adsorbent of the present invention does not interrupt a flow path of gas, a pressure loss is substantially decreased when the adsorbent of the present invention is used in a device such as an air cleaning device.

In addition, since the nanostructure formed on the adsorbent of the present invention is rigid in itself and is tightly coupled to the porous member, it does not have a problem of strength as activated carbon having an enlarged specific surface area, and is not likely to cause secondary contamination by, for example, generation of dust due to breaking of the adsorbent itself.

As described above, since the adsorbent of the present invention adsorbs a dramatically increased amount of a hazardous substance per unit volume (mass), the adsorbent can be made smaller and, as a result, a device such as an air cleaning device or a concentration sensor including the adsorbent can be made smaller.

Figure 2:
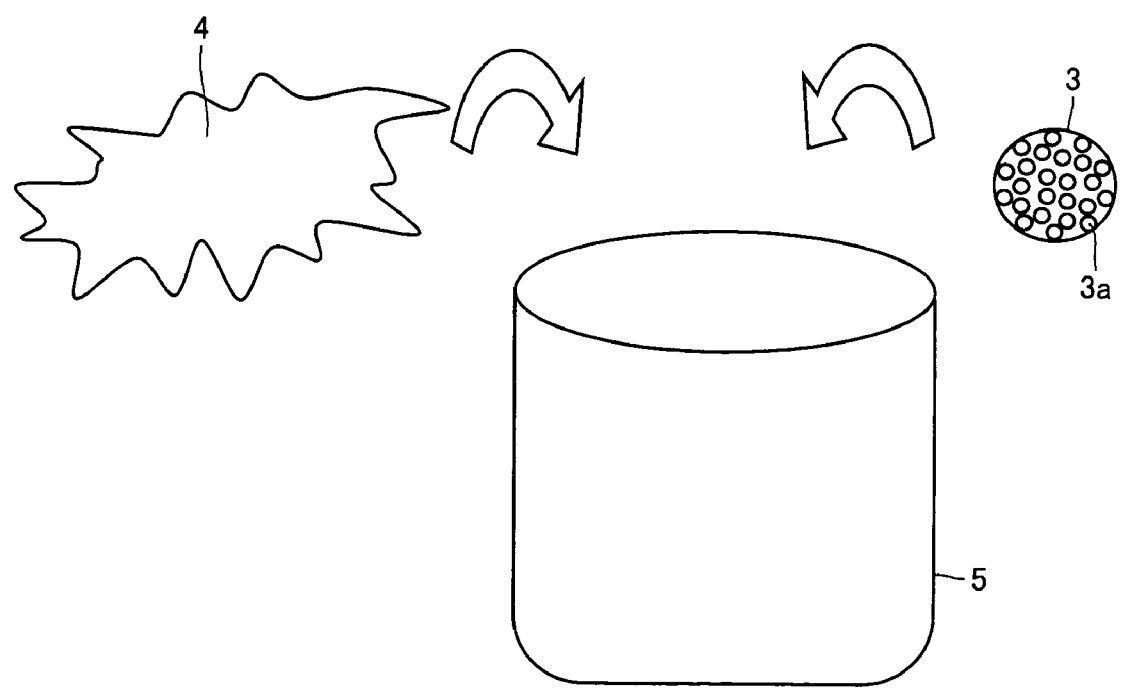
FIG. 2 is a schematic perspective view for describing a method of coating a surface of a porous member used in the present invention with catalyst particles.

The adsorbent of the present invention as described above is produced by, for example, a method as follows. As shown in FIG. 2, a liquid reagent 4 including catalyst particles is put in a container 5, and then porous member 3 is put in container 5. These components are agitated in container 5 to coat an outer surface of porous member 3 and inner surfaces of holes 3a with the catalyst particles.

By agitation of porous member 3 and reagent 4 inside container 5 using ultrasound or the like, not only the outer surface of porous member 3 but also the inner surfaces of holes 3a can be coated with the catalyst particles. Though coating with the catalyst particles can be performed by, for example, vacuum evaporation, electron beam evaporation or electroless plating, the agitation as described above is preferably performed particularly because the coating can be readily performed.

The method may include a step of cleaning porous member 3 with ultraviolet light to remove an impurity on a surface of porous member 3 before immersing porous member 3 in reagent 4 inside container 5. In this situation, it is preferable to use a dielectric barrier discharge excimer lamp device enclosing a Xe gas, for example, as a source of ultraviolet light and apply ultraviolet light having a central wavelength of 146 nm with an irradiance of 10 mW/cm$^2$ for about 1 hour.

Then, porous member 3 coated with the catalyst particles as above is placed in a plasma CVD apparatus, for example, and a gas as a material of the nanostructures is introduced to flow through the apparatus to generate plasma of the gas flowing in the apparatus to grow the nanostructures on the outer surface of porous member 3 and inner surfaces of holes 3a. Besides plasma CVD described above, nanostructures 1 can also be formed with thermal CVD or the like. Nanostructures 1 formed as such tend to grow with holding the catalyst particles on tips thereof. As a result, the adsorbent of the present invention as shown in FIG. 1 is produced.

As described above, at least a portion of the surface of the porous member can be coated with a metal such as the catalyst particles. In the present invention, however, at least a portion of the surface of the porous member may be coated with a magnetic material. With this, a mounting position of the adsorbent of the present invention can be controlled with a magnetic field, which results in an advantage that, for example, formation of a wasted space due to overlapping adsorbents can be avoided to increase an amount of the hazardous substance adsorbed per unit volume of the adsorbent. At least one of Ni, Fe and a rare-earth element, for example, can be used as the magnetic material.

Figure 3:
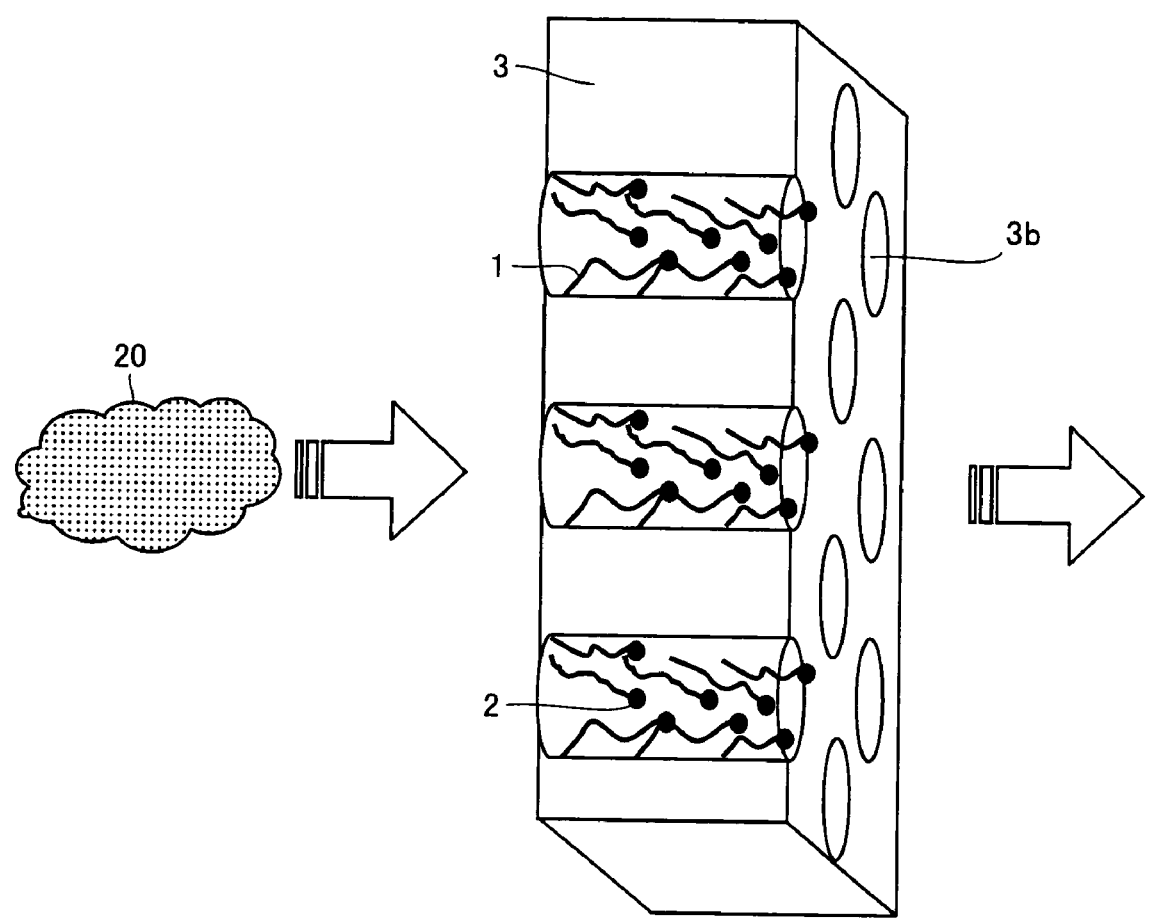
FIG. 3 is a schematic perspective view of a preferred example of a porous filter of the present invention.

FIG. 3 is a schematic perspective view of a preferred example of a porous filter of the present invention. The porous filter includes porous member 3, a fibrous nanostructure 1 formed inside a hole 3b penetrating porous member 3, and catalyst particle 2 attached to a surface of nanostructure 1 and held on a tip of nanostructure 1.

Nanostructure 1 may or may not have a hollow structure. Examples of a material which can be used to form nanostructure 1 include a carbon-based material such as a hollow carbon nanotube or a non-hollow carbon fiber or carbon nanowire (a fibrous carbon which is finer than a carbon fiber), a metal-based material such as Au, Ag or Ni, and a material such as $TiO_2$ or Si. Though nanostructure 1 is formed only on an inner surface of hole 3b in FIG. 3, it may also be formed on an outer surface of porous member 3.

Examples of a material which can be used to form porous member 3 include a metal oxide-based material such as $Al_2O_3$, $TiO_2$, $ZrO_2$, $Nb_2O_5$, $SnO_2$, $HfO_2$, or $AlPO_4$, a silicate-based material such as $SiO_2.Al_2O_3$, $SiO_2.TiO_2$, $SiO_2.V_2O_5$, $SiO_2.B_2O_3$, or $SiO_2.Fe_2O_3$, a metal-based material formed with Pt, Ag, Au, or the like, a semiconductor-based material formed with Si or the like, a carbon-based material formed with activated carbon, an organic polymer or the like, a material derived from a living body such as diatomaceous earth or a scallop shell, and $SiO_2$. Since porous member 3 is often heated to at least 200° C. when nanostructure 1 is formed on the surface of porous member 3, porous member 3 is preferably resistant to heat of at least 200° C. In addition, a shape of porous member 3 is not specifically limited, and porous member 3 may have, for example, a honeycomb shape.

Furthermore, though a diameter of an opening of hole 3b penetrating porous member 3 varies depending on the material forming porous member 3, when porous member 3 is formed with diatomaceous earth having a particle diameter of about 2-500 μm, for example, the diameter of the opening can be about 0.1-100 μm.

In addition, when nanostructure 1 is formed with the aforementioned carbon-based material, at least one of metals such as Fe, Ni, Co, Cr, Mo, W, Ti, Au, Ag, Cu, Pt, Ta, Al, Pd, Gd, Sm, Nd, and Dy, for example, can be used as a material to form catalyst particle 2. A diameter of catalyst particle 2 tends to control a diameter of fibrous nanostructure 1, that is, catalyst particle 2 having a smaller diameter tends to allow formation of fibrous nanostructure 1 having a smaller diameter by vapor phase epitaxy such as plasma CVD. Though catalyst particle 2 only held on the tip of nanostructure 1 is shown in FIG. 3, catalyst particle 2 may also be attached to a surface of nanostructure 1 other than the tip and a surface of porous member 3 (including the inner surface of hole 3b).

A hazardous substance 20 flows in a direction of an arrow shown in FIG. 3 into one surface of the porous filter of the present invention as described above. Hazardous substance 20 is contained in gas or liquid. Such hazardous substance 20 is adsorbed and removed by nanostructure 1 formed on the inner surface of hole 3b of the porous filter. Then, clean gas or liquid having hazardous substance 20 removed therefrom flows from an opposite surface of the porous filter. Examples of hazardous substance 20 include an aldehyde such as formaldehyde, a VOC (Volatile Organic Compound) such as toluene or xylene, carbon monoxide, carbon dioxide, acetic acid, ammonia, and a sulfur-containing substance.

It is expected that the porous filter of the present invention as described above efficiently removes hazardous substance 20.

That is, when gas including a hazardous substance is circulated at a constant speed, for example, only a small surface area of conventionally used activated carbon contacts and reacts with flowing gas or liquid per unit time, because activated carbon have to capture molecules into pores formed therein. In contrast, since most of a surface of the nanostructure formed on the porous filter of the present invention is a region which can directly contact gas or liquid including a hazardous substance, more hazardous substance can be contacted and an adsorption speed also substantially increases.

Furthermore, in contrast to the pores of activated carbon, since the nanostructure formed on the porous filter of the present invention does not interrupt a flow path of gas or liquid, a pressure loss is substantially decreased when the porous filter of the present invention is used in a device such as an air cleaning device.

In addition, since the nanostructure formed on the porous filter of the present invention is rigid in itself and is tightly coupled to the porous member, it does not have a problem of strength as activated carbon having an enlarged specific surface area, and is not likely to cause secondary contamination by, for example, generation of dust due to breaking of the porous filter itself.

Figure 4:
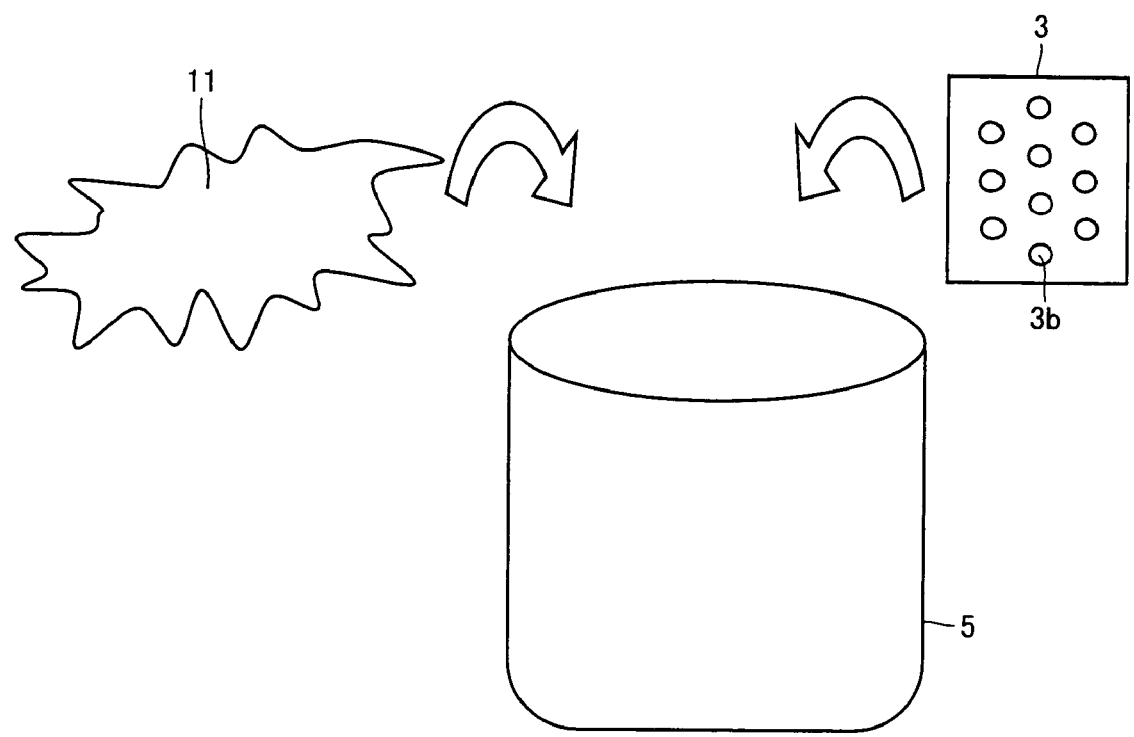
FIG. 4 is a schematic perspective view for describing a method of coating a surface of a porous member with catalyst particles in the present invention.

The porous filter of the present invention as described above is produced by, for example, a method as follows. As shown in FIG. 4, a liquid reagent 11 including catalyst particles is put in a container 5, and then porous member 3 is put in container 5. These components are agitated in container 5 to coat an outer surface of porous member 3 and an inner surface of hole 3b with the catalyst particles.

By agitation of porous member 3 and reagent 11 inside container 5 using ultrasound or the like, not only the outer surface of porous member 3 but also the inner surface of hole 3b can be coated with the catalyst particles. The outer surface of porous member 3 and the inner surface of hole 3b can also be evenly coated with the catalyst particles by dispersing the catalyst particles in a superheated water vapor and then spraying onto porous member 3. The superheated water vapor used in the present invention means a water vapor having a temperature higher than 100° C. at 1 atmospheric pressure. The superheated water vapor can be generated by, for example, superheating vaporized water molecules with a heat source to a temperature higher than 100° C. at 1 atmospheric pressure. Though coating with the catalyst particles can be performed by, for example, vacuum evaporation, electron beam evaporation or electroless plating, the agitation as described above is preferably performed particularly because the coating can be readily performed.

The method may include a step of cleaning porous member 3 with ultraviolet light to remove an impurity on a surface of porous member 3 before immersing porous member 3 in reagent 11 inside container 5. In this situation, it is preferable to use the dielectric barrier discharge excimer lamp device enclosing a Xe gas, for example, as a source of ultraviolet light and apply ultraviolet light having a central wavelength of 146 nm with an irradiance of 10 mW/cm$^2$ for about 1 hour.

Then, porous member 3 coated with the catalyst particles as above is placed in a plasma CVD apparatus, for example, and a gas as a material of the nanostructure is introduced to flow through the apparatus to generate plasma of the gas flowing in the apparatus to grow nanostructure 1 shown in FIG. 3. Besides plasma CVD described above, nanostructure 1 can also be formed with thermal CVD or the like. Nanostructure 1 formed as such tends to grow with holding the catalyst particle on a tip thereof.

Figure 5:
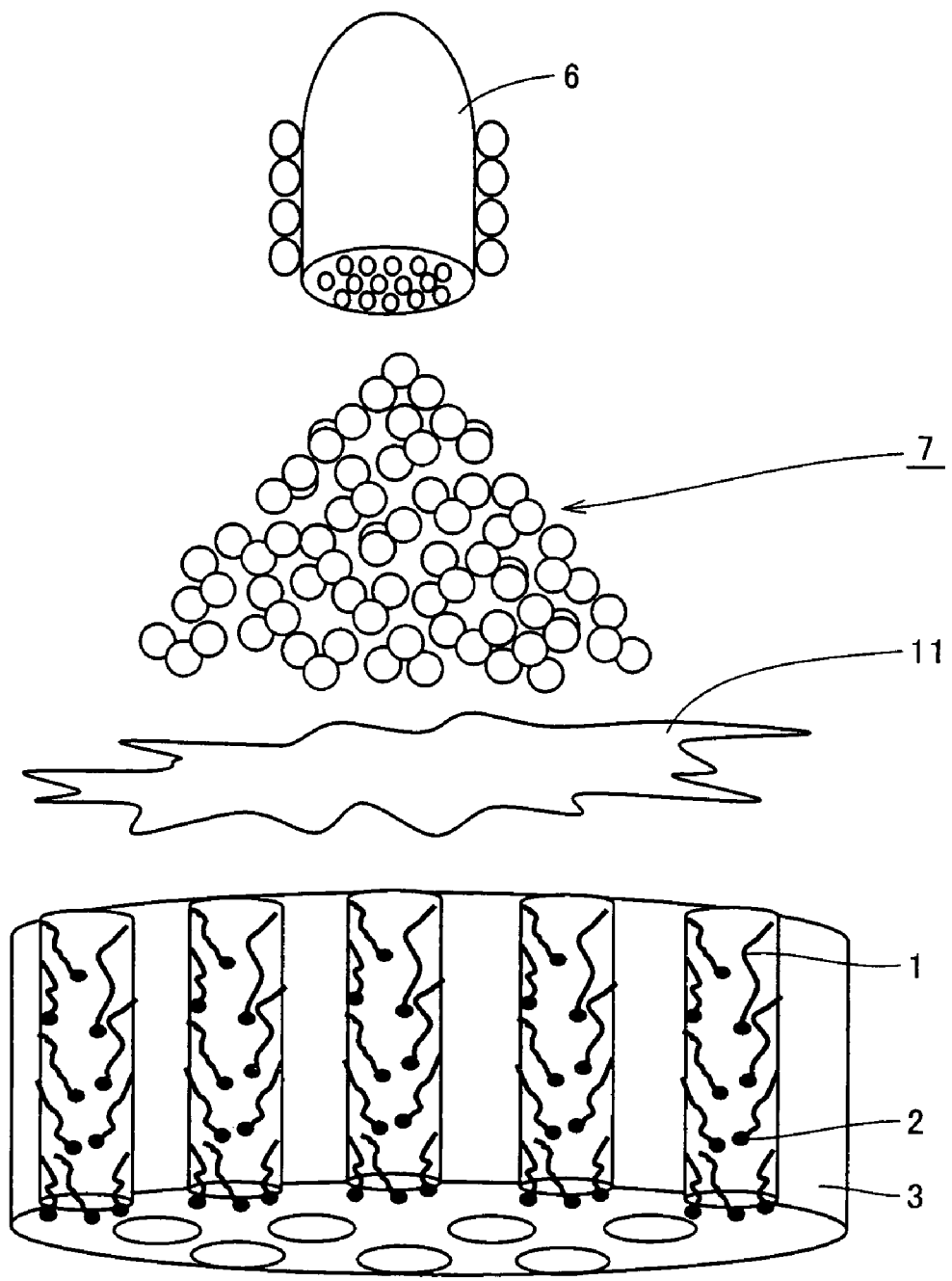
FIG. 5 is a schematic perspective view for describing a method of coating a surface of a nanostructure with catalyst particles in the present invention.

Thereafter, as shown in a schematic perspective view of FIG. 5, a superheated water vapor 7 is ejected from a superheated water vapor jet device 6 to spray superheated water vapor 7 over liquid reagent 11 including catalyst particles to allow the catalyst particles to be contained in a dispersion gas including superheated water vapor 7. Then, the dispersion gas containing the catalyst particles is sprayed on a surface of porous member 3 having nanostructure 1 grown thereon to attach the catalyst particle in the dispersion gas to the surface of nanostructure 1. As a result, the porous filter of the present invention as shown in FIG. 3 can be produced. Though use of the dispersion gas including the superheated water vapor is not a limitation in the present invention, the superheated water vapor is preferably used because a liquid component of the liquid reagent including the catalyst particles can be thermally removed with high thermal energy. In addition, a metal similar to that used for coating described above, that is, at least one of metals such as Fe, Ni, Co, Cr, Mo, W, Ti, Au, Ag, Cu, Pt, Ta, Al, Pd, Gd, Sm, Nd, and Dy, for example, can be used as the catalyst particles included in reagent 11.

Figure 6:
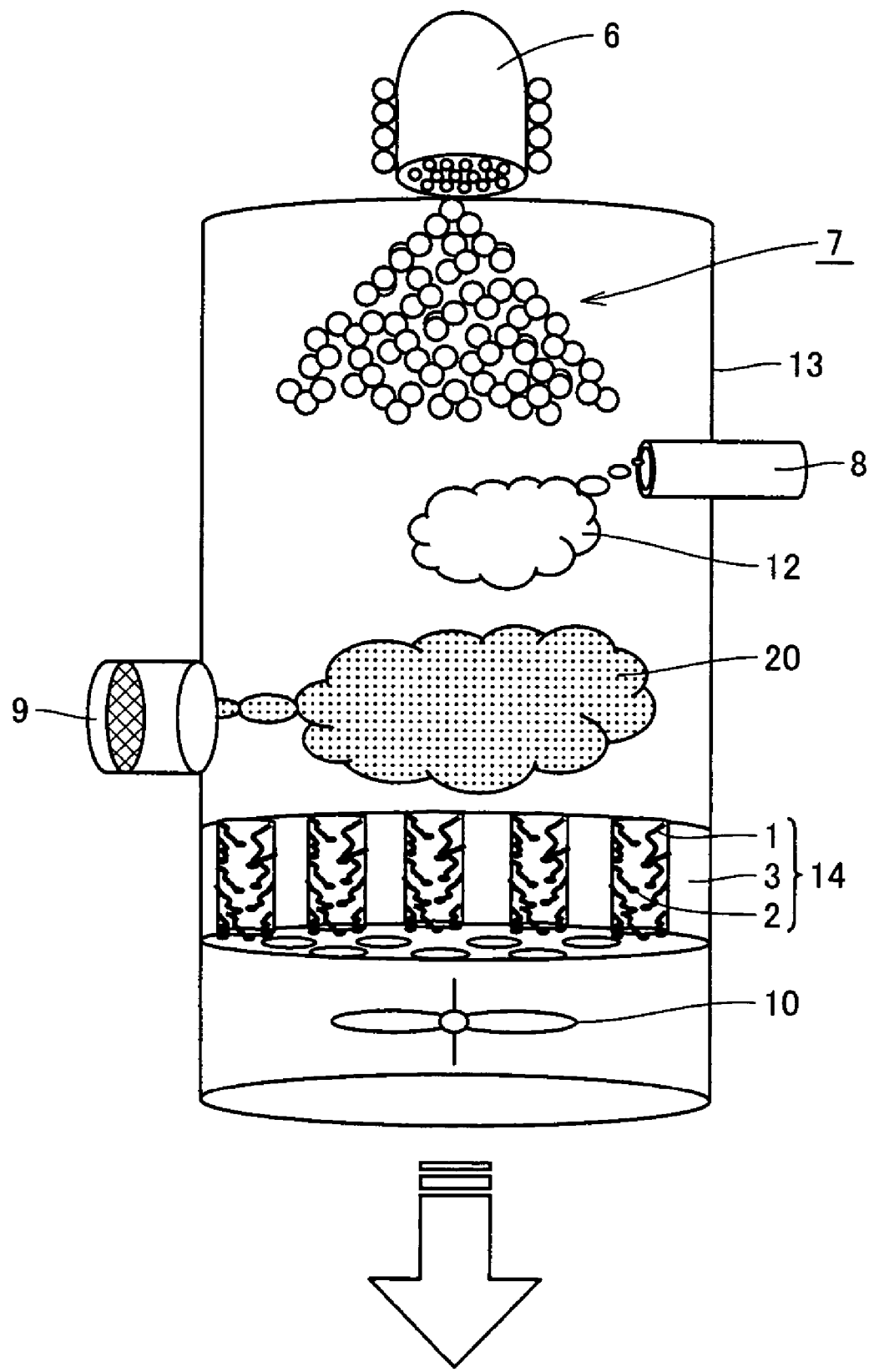
FIG. 6 is a schematic perspective view of a preferred example of an air cleaning device of the present invention.

FIG. 6 is a schematic perspective view of a preferred example of an air cleaning device of the present invention. The air cleaning device includes a reaction chamber 13, superheated water vapor jet device 6, a decomposition acceleration gas inlet 8, an outside air inlet 9, a porous filter 14 of the present invention, and an agitator 10. Hazardous substance 20 flowing from outside air inlet 9 into reaction chamber 13 is efficiently adsorbed by nanostructure 1 in porous filter 14. An amount and a speed of adsorption of hazardous substance 20, however, are saturated with time. Then, superheated water vapor 7 is ejected from superheated water vapor jet device 6 and a decomposition acceleration gas 12 is introduced from decomposition acceleration gas inlet 8 into superheated water vapor 7 to generate a decomposition gas including superheated water vapor 7 and decomposition acceleration gas 12, and the decomposition gas is sprayed on a surface of porous filter 14 to allow hazardous substance 20 adsorbed by nanostructure 1 in porous filter 14 to be decomposed and removed. A decomposition product of hazardous substance 20 is agitated by agitator 10 and then ejected from the air cleaning device (in a direction indicted by an arrow shown in FIG. 6).

In the air cleaning device shown in FIG. 6, though the hazardous substance adsorbed by the nanostructure can be decomposed only by thermal energy of the superheated water vapor without using the decomposition acceleration gas, since a temperature of the air cleaning device may become substantially high in this situation, the decomposition acceleration gas is preferably used to decompose the hazardous substance at a lower temperature. An alcohol such as ethanol, or oxygen, for example, can be used as the decomposition acceleration gas. In addition, outside air inlet 9 in the air cleaning device shown in FIG. 6 can include, for example, an HEPA filter for preventing dust.

EXAMPLE 1

Diatomaceous earth (produced by Showa Chemical Industry Co., Ltd.) including at least 85 mass % of $SiO_2$ as a main component was used as a porous member. The porous member had a particle diameter of 10 μm, and a plurality of holes formed in the porous member had an average diameter of about 1 μm.

First, a dielectric barrier discharge excimer lamp device enclosing a Xe gas was used to irradiate a surface of the porous member with ultraviolet light having a central wavelength of 146 nm with an irradiance of 10 mW/cm$^2$ for 1 hour to remove a contaminant on the surface of the porous member.

Then, Ni paste (produced by Nippon Paint Co., Ltd.) including Ni particles having diameters of about 10 nm and the porous member irradiated with ultraviolet light were put in an acetone solvent inside a container, and were agitated by application of ultrasound into the container.

After agitation, the porous member was removed from the container and placed in a vacuum chamber (a microwave plasma CVD (MPCVD) apparatus). A vacuum pump was used to exhaust air until a pressure inside the vacuum chamber became $1 \times 10^{-5}$ Pa, and then heat treatment of the porous member was performed at 600° C. for 30 minutes. In an experiment separately performed under the same condition, a cross section after the heat treatment was examined with a transmission electron microscope (TEM). As a result, it became apparent that the surface of the porous member was substantially evenly coated with Ni particles with a thickness of 50 nm.

Thereafter, nanostructures were grown on the surface of the porous member coated with Ni particles. While a temperature of a substrate placed in the MPCVD apparatus was maintained at 600° C. and a pressure inside the vacuum chamber was adjusted to about 15 Torr with a pressure control valve, an $H_2$ gas of 80 sccm was introduced into the vacuum chamber through a mass flow controller, and then a microwave of 2.45 GHz (350 W) was introduced to set the $H_2$ gas to a plasma state to clean the surface of the porous member mounted on the substrate for about 5 minutes.

Then, the $H_2$ gas of 80 sccm and a $CH_4$ gas of 20 sccm were introduced into the vacuum chamber, and the microwave of 2.45 GHz (500 W) was further introduced. With this, a material gas formed with the $H_2$ gas and the $CH_4$ gas was set to a plasma state, and the porous member on the substrate was exposed to the plasma for 10 minutes. In this step, a bias voltage of −100 V was applied to the substrate on which the porous member was mounted. As a result, fibrous nanostructures, each formed with carbon and having the Ni particle on a tip thereof, were grown from an outer surface of the porous member and inner surfaces of a plurality of holes formed in the porous member to produce an adsorbent of the present invention. Each of the nanostructures in the adsorbent of the present invention had a diameter of 10-30 nm and a length of 1-50 μm. In addition, the nanostructures included non-hollow carbon fibers and hollow carbon nanotubes in a ratio of about 1:1. States of the nanostructures were examined using the TEM or a scanning electron microscope (SEM). An amount of Ni particles used was 5 mg, and 1.5 mg of nanostructures were obtained. It is to be noted that, an amount of Ni particles included in the Ni paste is correlated with a number of nanostructures grown. Therefore, it is preferable to increase the amount of Ni particles to increase the number of nanostructures grown and increase a yield of the adsorbent.

EXAMPLE 2

A substrate was formed as follows. On a (111) plane of Si substrate having a silicon oxide film having a thickness of 30 nm formed thereon, an Si thin film having a thickness of 10 nm was formed. Thereafter, Ni thin films as pattern electrodes, each having a square shape of 3 μm per side and a thickness of 100 nm, were formed on both ends of the Si thin film.

The substrate was then placed in the MPCVD apparatus used in example 1, and a temperature of the substrate was maintained at 800° C. Thereafter, a pressure inside the vacuum chamber was adjusted to about 15 Torr with the pressure control valve, the $H_2$ gas of 80 sccm was introduced through the mass flow controller, and then the microwave of 2.45 GHz (350 W) was introduced to set the $H_2$ gas to a plasma state to clean a surface of the substrate for about 5 minutes.

Then, the $H_2$ gas of 80 sccm and the $CH_4$ gas of 20 sccm were introduced into the vacuum chamber, the microwave of 2.45 GHz (500 W) was further introduced to set the material gas formed with the $H_2$ gas and the $CH_4$ gas to a plasma state, and the surface of the substrate was exposed to the plasma for 15 minutes. In this step, a bias voltage of −100 V was applied to the substrate. As a result, a conductive nanowire having a width of 10 nm and a length of 60 μm was produced.

Both sides of the conductive nanowire were electrically connected to respective pattern electrodes, and a voltage of 0.5 V was applied between the electrodes to flow a current of 10 μA through the conductive nanowire to generate a magnetic field on a surface of the conductive nanowire. Utilizing the magnetic field, the adsorbent of example 1 could be successfully arranged on the surface of the conductive nanowire.

Though only one conductive nanowire was electrically connected in example 2 for simplifying measurement of an arrangement of the adsorbent on the conductive nanowire, when this mechanism is applied to a device, a larger effect is expected when a larger number of conductive nanowires are electrically connected between the pattern electrodes.

EXAMPLE 3

Figure 7:
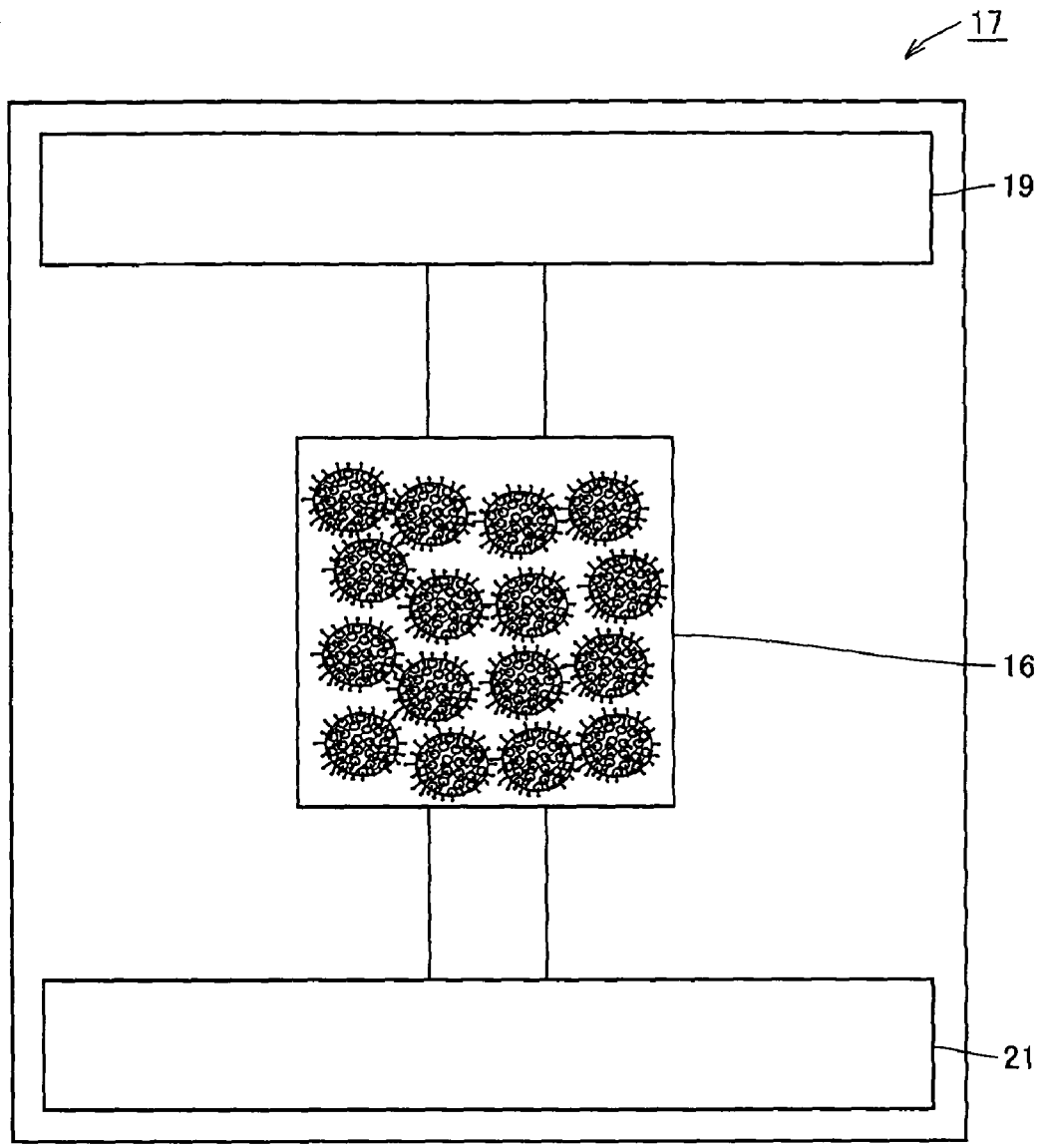
FIG. 7 is a schematic side perspective view of an air cleaning device used in an example 3 of the present invention.

In a stainless case 16 of an air cleaning device 17 shown in FIG. 7, 0.03 g of the adsorbent of example 1 was housed. Air cleaning device 17 was then intentionally placed in an apparatus of 1 $m^3$ containing diffused toluene of 10 ppm to introduce air inside the apparatus from an air inlet 19 and eject cleaned air from an air outlet 21. A concentration of toluene inside the apparatus was measured at every prescribed time, and a variation in the concentration of toluene over time was evaluated. A result is shown in Table 1. The concentration of toluene inside the apparatus shown in Table 1 was calculated by analyzing composition of gas inside the apparatus using gas chromatography.

TABLE 1

|  | Time (min) | | |
| --- | --- | --- | --- |
|  | 0 | 5 | 10 |
| Concentration of Toluene Inside Apparatus (ppm) | 10 | 0.09 | 0.001 |

Considering a fact that the concentration of 10 ppm corresponded to 0.0376 g of toluene, it became apparent from the result shown in Table 1 that about 1.25 g of toluene could be adsorbed per 1 g of the adsorbent of example 1. In contrast to conventional fibrous activated carbon which can adsorb 0.1 g of toluene per 1 g thereof, the adsorbent of example 1 has a high adsorption property.

EXAMPLE 4

Porous alumina ("ANODISK47" produced by Whatman) formed by anodic oxidation of an aluminum film in an acid solution was used as the porous member. The porous member had a diameter of 43 mm and a thickness of 60 μm, and openings of a plurality of holes penetrating the porous member had an average diameter of about 0.2 μm.

First, the dielectric barrier discharge excimer lamp device enclosing a Xe gas was used to irradiate a surface of the porous member with ultraviolet light having a central wavelength of 146 nm with an irradiance of 10 mW/$cm^2$ for 1 hour to remove a contaminant on the surface of the porous member.

Then, Ni paste (produced by Nippon Paint Co., Ltd.) including a plurality of Ni particles having diameters of about 10 nm and the porous member irradiated with ultraviolet light were put in an acetone solvent inside a container, and were agitated by application of ultrasound into the container.

After agitation, the porous member was removed from the container and moved into the vacuum chamber (the microwave plasma CVD (MPCVD) apparatus). The vacuum pump was used to exhaust air until a pressure inside the vacuum chamber became $1 \times 10^{-5}$ Pa, and then heat treatment of the porous member was performed at 600° C. for 30 minutes. In an experiment separately performed under the same condition, a cross section after the heat treatment was examined with the transmission electron microscope (TEM). As a result, it became apparent that the surface of the porous member was substantially evenly coated with Ni particles with a thickness of 50 nm.

Thereafter, nanostructures were grown on the surface of the porous member coated with Ni particles. While a temperature of a substrate placed in the MPCVD apparatus was maintained at 600° C. and a pressure inside the vacuum chamber was adjusted to about 15 Torr with a pressure control valve, the $H_2$ gas of 80 sccm was introduced into the vacuum chamber through the mass flow controller, and then the microwave of 2.45 GHz (350 W) was introduced to set the $H_2$ gas to a plasma state to clean the surface of the porous member mounted on the substrate for about 5 minutes.

Then, the $H_2$ gas of 80 sccm and the $CH_4$ gas of 20 sccm were introduced into the vacuum chamber, and the microwave of 2.45 GHz (500 W) was further introduced. With this, the material gas formed with the $H_2$ gas and the $CH_4$ gas was set to a plasma state, and the porous member on the substrate was exposed to the plasma for 10 minutes. In this step, a bias voltage of −100 V was applied to the substrate on which the porous member was mounted. As a result, a plurality of fibrous nanostructures, each formed with carbon and having the Ni particle on a tip thereof, were grown from a whole outer surface of the porous member and inner surfaces of a plurality of holes formed in the porous member. Each of the nanostructures grown had a diameter of 10-30 nm and a length of 1-50 μm. In addition, the nanostructures included non-hollow carbon fibers and hollow carbon nanotubes in a ratio of about 1:1. States of the nanostructures were examined using the TEM or the scanning electron microscope (SEM). An amount of Ni particles used was 5 mg, and 1.5 mg of nanostructures were obtained. It is to be noted that, an amount of Ni particles included in the Ni paste is correlated with a number of nanostructures grown. Therefore, it is preferable to increase the amount of Ni particles to increase the number of nanostructures grown and increase a yield of the adsorbent.

The porous member having nanostructures obtained as above was placed in a chamber including a superheated water vapor generation mechanism. The superheated water vapor generation mechanism generated a superheated water vapor of 500° C. by generating saturated water as a saturated water vapor with a small boiler and then passing the saturated water vapor through a metal pipe heated with dielectric heating for superheating. The superheated water vapor of 500° C. generated with the superheated water vapor generation mechanism was ejected from a superheated water vapor jet device with a pressure of 2 kg/cm² to introduce an acetone solvent containing the aforementioned Ni paste (produced by Nippon Paint Co., Ltd.) into the superheated water vapor, and the superheated water vapor was then sprayed onto the surface of the porous member having the nanostructures for 10 seconds to produce a porous filter. Ni particles attached to a surface of the nanostructure of the porous filter in a film-like form were observed with the TEM and SEM.

States of Ni particles attached to the surface of the nanostructure when jet pressures (pressures for jetting) of the superheated water vapor of 500° C. in the superheated water vapor jet device were set to 0.1 kg/cm², 0.5 kg/cm², 1 kg/cm², 2 kg/cm², 5 kg/cm², and 10 kg/cm², respectively, were observed with the TEM and SEM. Results are shown in Table 2.

TABLE 2

| | Jet Pressure (kg/cm²) | | | | | |
|---|---|---|---|---|---|---|
| | 0.1 | 0.5 | 1 | 2 | 5 | 10 |
| State of Ni Particles | Agglomerated | Agglomerated | Film-Like | Film-Like | Rather Sparse | Sparse |

As shown in Table 2, jet pressures of the superheated water vapor of 1 kg/cm² and 2 kg/cm² in the superheated water vapor jet device were preferable because Ni particles were attached to the surface of the nanostructure in a film-like form. It is to be noted that, an "agglomerated" state of Ni particles in Table 2 means that an excessively large amount of Ni particles in a ratio of $10^{10}$-$100^{10}$/cm² were attached in a grain-like form forming large projections and depressions on the surface. In addition, a "rather sparse" state of Ni particles in Table 2 means that Ni particles were not attached in a film-like form since an amount of attached Ni particles was as small as 1-$5^{10}$/cm². A "sparse" state of Ni particles in Table 2 means that Ni particles were not attached in a film-like form since an amount of attached Ni particles was excessively small, that is, less than 1/cm².

EXAMPLE 5

Cleaning of air including formaldehyde was performed using the air cleaning device of the present invention shown in FIG. 6. First, porous filter 14 obtained in example 4 was placed in stainless reaction chamber 13 including superheated water vapor jet device 6, decomposition acceleration gas inlet 8, outside air inlet 9, and agitator 10 shown in FIG. 6 to form an air cleaning device.

Then, dry air including 0.155 ppm of formaldehyde was introduced from outside air inlet 9 into reaction chamber 13 at a flow rate of 1 cc/min, and gas passed through porous filter 14 was collected in a collection tube for 10 minutes. In this step, the superheated water vapor was not ejected from superheated water vapor jet device 6, and the decomposition acceleration gas was also not introduced from decomposition acceleration gas inlet 8. A concentration of formaldehyde in collected gas was calculated by a method of DNPH derivative solid phase adsorption/solvent extraction-high performance liquid chromatography. The method includes steps of passing gas collected as above through a DNPH silica gel column to fix formaldehyde to the column, eluting formaldehyde with an acetonitrile solvent, and analyzing an amount of formaldehyde in an obtained solution using high performance liquid chromatography. The concentration of formaldehyde in the collected gas calculated by the method was 0.08 ppm. This means that 1.5 mg of the nanostructures adsorbed 90 μg of formaldehyde, that is, 60 mg of formaldehyde could be adsorbed per 1 g of the nanostructures. In addition, an adsorption speed for formaldehyde was about 6 mg/g per minute, which showed that adsorption efficiency was dramatically improved as compared to an adsorbent using activated carbon.

For estimation of a pressure loss, dry air was introduced into reaction chamber 13 shown in FIG. 6 at a flow rate of 1 m/second, and a difference in pressures at an inlet and an outlet was measured. The difference in pressures was about 3 Pa, which was much smaller than a pressure difference of 50 Pa measured with fibrous activated carbon under the same condition.

Thereafter, superheated water vapor 7 of 300° C. was ejected from superheated water vapor jet device 6, dry air containing 0.1 ppm of ethanol as decomposition acceleration gas 12 was introduced in reaction chamber 13, then dry air containing 0.155 ppm of formaldehyde was introduced from outside air inlet 9 into reaction chamber 13 at a flow rate of 1 cc/min, and gas passed through porous filter 14 was collected in a collection tube for 10 minutes. A concentration of formaldehyde in collected gas was measured by the above-described method of DNPH derivative solid phase adsorption/solvent extraction-high performance liquid chromatography. As a result, the concentration was not more than a detection limit of the high performance liquid chromatography. Therefore, formaldehyde was probably decomposed to carbon dioxide and water in the presence of catalyst particles attached to nanostructures 1, superheated water vapor 7 and decomposition acceleration gas 12.

EXAMPLE 6

Dispersion gas including the superheated water vapor was ejected with a jet pressure of 2 kg/cm$^2$ for 10 seconds to a surface of a porous member formed with porous alumina having a diameter of 43 mm, a thickness of 60 μm and an average diameter of openings of a plurality of penetrating holes of 200 nm. The dispersion gas was prepared by introducing into the superheated water vapor 20 ml of a toluene solvent containing a plurality of Pt particles (produced by Nippon Paint Co., Ltd.) having a particle diameter of about 3 nm to disperse the Pt particles therein. The porous member processed as such was termed sample A.

In addition, the dispersion gas having the same composition as above was ejected in the same condition as above to a surface of the porous member formed with porous alumina having a diameter of 43 mm, a thickness of 60 μm and an average diameter of openings of a plurality of penetrating holes of 200 nm, and having fibrous nanostructures formed with carbon grown in a ratio of 10$^{11}$/cm$^2$ on inner surfaces of the holes. A porous filter produced as such was termed sample B. Each of nanostructures in sample B had a diameter of 10-30 nm and a length of 1-50 μm.

Each of sample A and sample B was then set in a stainless housing placed in an estimation chamber having a volume of 1 m$^3$. Thereafter, the superheated water vapor of 300° C. was introduced into the estimation chamber, dry air including toluene as a hazardous substance was introduced at a flow rate of 1 cc/min, and gas was collected in a collection tube for 1 minute on an outlet side of the estimation chamber. A concentration of toluene in the gas collected was calculated using a known measurement method which is a combination of solid phase adsorption/thermal desorption and gas chromatograph/mass spectrometry. Results are shown in Table 3.

TABLE 3

|  | Sample A | Sample B |
|---|---|---|
| Concentration of Toluene Inside Estimation Chamber (ppm) | 0.1 | Not More Than Detection Limit |

As shown in Table 3, it is ensured that sample B having nanostructures formed on inner surfaces of holes penetrating porous alumina and Pt particles as catalyst particles attached to surfaces of the nanostructures has a higher effect of removing toluene as compared to sample A not having nanostructures formed thereon.

Although the present invention has been described and illustrated in detail, it is clearly understood that the same is by way of illustration and example only and is not to be taken by way of limitation, the spirit and scope of the present invention being limited only by the terms of the appended claims.

What is claimed is:
1. A porous filter, comprising:
   a porous member having a plurality of holes; and
   a nanostructure formed on an interior hole surface of said porous member.
2. The porous filter according to claim 1, wherein said nanostructure is formed with carbon.
3. The porous filter according to claim 1, wherein said porous member is resistant to heat of at least 200° C.
4. An air cleaning device comprising the porous filter according to claim 1.
5. A method of cleaning air, comprising the step of
   decomposing a hazardous substance using a porous filter and a decomposition gas including a superheated water vapor,
   wherein the porous filter has a porous member with a plurality of holes, and
   a nanostructure formed on at least a portion of a surface of said porous member.
6. The method of cleaning air according to claim 5, wherein said decomposition gas contains a decomposition acceleration gas.
7. A porous filter, comprising:
   a porous member having a plurality of holes; and
   a nanostructure formed on an interior hole surface of said porous member,
   wherein the nanostructure filters a volume of air passing through the holes.

* * * * *